United States Patent [19]

Harju et al.

[11] 4,389,336
[45] Jun. 21, 1983

[54] PREPARATION OF NAPHTHALENE-OXIDATION CATALYST BY IMPREGNATION OF SILICA WITH AQUEOUS SOLUTION OF $VOC_2O_4$—$K_2SO_4$—$KHSO_4$

[75] Inventors: Philip H. Harju, Spring Church; Eugene A. Pasek, Export, both of Pa.

[73] Assignee: Koppers Company, Inc., Pittsburgh, Pa.

[21] Appl. No.: 303,169

[22] Filed: Sep. 17, 1981

[51] Int. Cl.³ .............................................. B01J 27/02
[52] U.S. Cl. ..................................... 252/440; 549/248
[58] Field of Search ........................................ 252/440

[56] References Cited

U.S. PATENT DOCUMENTS

| | | | |
|---|---|---|---|
| 1,880,678 | 10/1932 | Beardsley et al. | 252/440 |
| 2,698,330 | 12/1954 | Fogate et al. | 252/440 X |
| 2,973,371 | 2/1961 | Chomitz et al. | 252/440 X |
| 3,167,567 | 1/1965 | Nonnenmacher et al. | 549/249 |
| 3,215,644 | 11/1965 | Kakenoki et al. | 252/440 |
| 3,352,887 | 11/1967 | Riley et al. | 549/249 |
| 3,507,810 | 4/1970 | Sanborn et al. | 549/249 X |
| 4,184,980 | 1/1980 | Sherif et al. | 252/436 |

FOREIGN PATENT DOCUMENTS

| | | |
|---|---|---|
| 245247 | 6/1963 | Australia . |
| 49-31630 | 8/1974 | Japan . |
| 633594 | 8/1965 | U.S.S.R. ............. 252/440 |
| 685325 | 12/1975 | U.S.S.R. ............. 252/440 |

Primary Examiner—Delbert E. Gantz
Assistant Examiner—William G. Wright
Attorney, Agent, or Firm—J. Timothy Keane; Donald M. MacKay; Herbert J. Zeh, Jr.

[57] ABSTRACT

Catalytic material is prepared by impregnating porous silica with an aqueous solution containing vanadyl oxalate ($VOC_2O_4$), potassium sulfate ($K_2SO_4$) and potassium bisulfate ($KHSO_4$). A free-flowing dry-appearing powder is provided comprising particles having substantially all compounds deposited from the impregnating solution attached to the silica particles within pores of the particles. Subsequent calcining of the powder provides a mixture of compounds within the particle pores containing at least one oxide of vanadium and at least one sulfate of potassium. Catalytic material prepared by the disclosed process is characterized in having a substantially uniform concentration of deposited compounds within the pores of the silica support. The catalytic material is particularly useful in a process for fluid bed oxidation of naphthalene to phthalic anhydride, in which oxidation process the catalyst provides high product yield at a low catalyst attrition rate.

29 Claims, 2 Drawing Figures

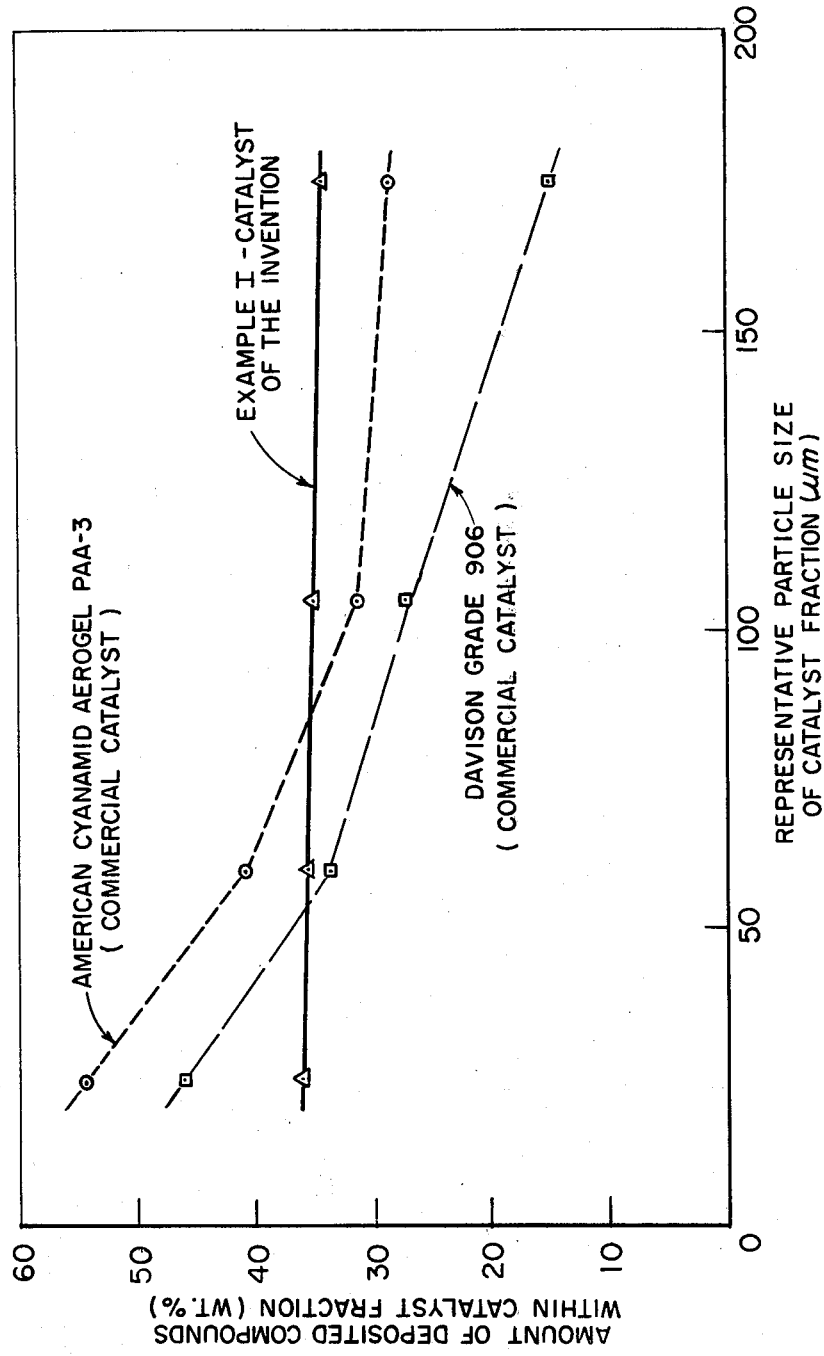

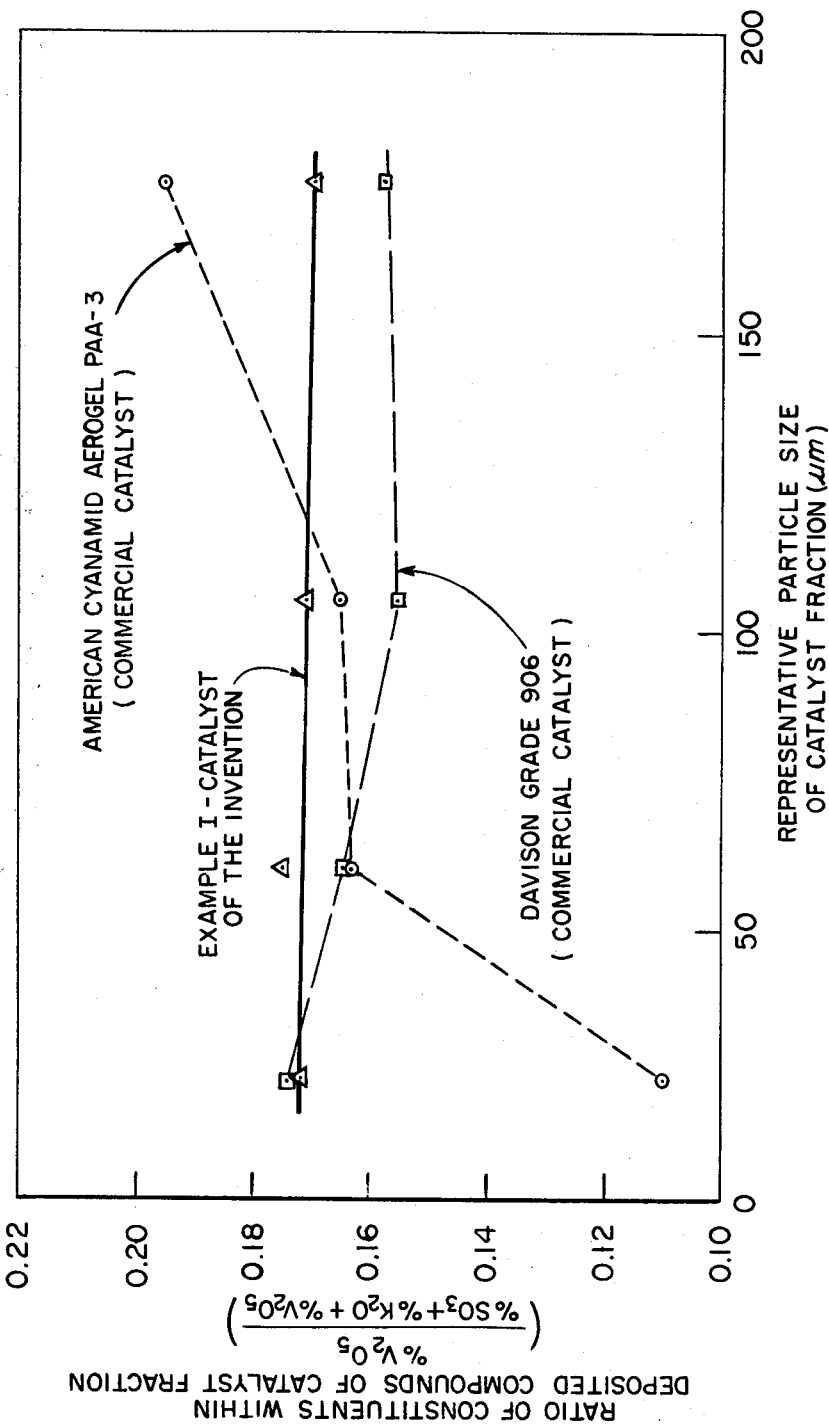

PREPARATION OF NAPHTHALENE-OXIDATION CATALYST BY IMPREGNATION OF SILICA WITH AQUEOUS SOLUTION OF VOC₂O₄—K₂SO₄—KHSO₄

BACKGROUND OF THE INVENTION

1. Field of the Invention

There are many well-known methods for preparing catalysts composed of vanadium-containing compounds deposited upon silicious support materials. Of particular interest herein are methods for preparing catalytic materials composed of one or more oxides of vanadium and one or more sulfates of potassium deposited upon silica support, which catalysts are useful in the oxidation of hydrocarbons to phthalic anhydride.

2. State of the Art

A catalyst for fluid bed oxidation of o-xylene or naphthalene to phthalic anhydride is described in U.S. Pat. No. 3,167,567 to Nonnenmacher et al. The catalyst is prepared by adding vanadium pentoxide to a molten solution of pyrosulfates formed by fusing either potassium pyrosulfate or potassium hydrogen sulfate, or a mixture thereof, then cooling the melt and grinding it to a powder, and thereafter mixing and heating the powder with silica gel to form $V_2O_5$—$K_2S_2O_7$—$Na_2S_2O_7$—$SiO_2$ catalyst. U.S. Pat. No. 3,352,887 to Riley et al. describes a naphthalene oxidation catalyst prepared by forming a melt of vanadium pentoxide and potassium pyrophosphate, which is cooled, ground to a powder and then added to silica gel to form a mixture; heating of the mixture fuses the silica gel and powder. U.S. Pat. No. 3,507,810 to Sanborn et al. describes a naphthalene oxidation catalyst prepared from an aqueous slurry of silica, potassium sulfate and ammonium metavanadate, which slurry is then spray-dried and calcined. A naphthalene-to-phthalic anhydride fluid bed oxidation catalyst, described in Japanese patent publication No. 31630 dated Aug. 23, 1974 of Saito et al., is prepared by mixing a colloidal silica sol with a vanadyl oxalate-potassium sulfate solution to form a slurry, which slurry is subsequently spray-dried and calcined to yield spherical catalyst particles.

A method for preparing a sulfur dioxide-to-sulfur trioxide oxidation catalyst is described in U.S. Pat. No. 4,184,980 to Sherif et al.; the method comprises impregnating a porous diatomaceous-earth support with a potassium sulfate-vanadyl sulfate solution, that solution derived by passing sulfur dioxide gas into an aqueous mixture of vanadium oxide, sulfuric acid and a potassium salt, a typical potassium salt being a sulfate, an oxalate, or a formate of potassium. A similar oxidation catalyst is described in Australian Pat. No. 245,247 to Davies; the catalyst is prepared by incorporating a vanadium compound into a silica gel, with the vanadium compound provided by a soluble vanadyl oxy-salt, such as vanadyl oxalate, vanadyl sulfate, vanadyl acetate and ammonium vanadate.

The foregoing catalysts or preparation methods are characterized by one or more disadvantages, such as requiring multi-step impregnations, utilizing unstable impregnation solutions, or in yielding catalysts that lack uniformity in composition, have low activity, require long conditioning periods, or have high attrition rates.

SUMMARY OF THE INVENTION

Fluidizable catalytically-active material is provided by a mixture of compounds deposited upon a silica support. This material is prepared by a process which comprises a step of impregnating porous silica xerogel support with an aqueous solution of salts comprising vanadyl oxalate ($VOC_2O_4$), potassium sulfate ($K_2SO_4$) and potassium bisulfate ($KHSO_4$). It is a characterizing feature of the process that the impregnating step provides a free-flowing dry-appearing powder comprised of particles having substantially all of the salts which are deposited from the impregnating solution attached to the support particles within pores of the particles. Subsequent calcining of the powder particles provides a mixture of deposited compounds within the particle pores, which mixture of deposited compounds consists essentially of at least one oxide-of-vanadium constituent and at least one sulfate-of-potassium constituent. The presence of significant amounts of other substances within the deposited compounds or within the silica xerogel support may decrease the selectivity of the catalytic material.

Catalytic material prepared by the process described herein is characterized in comprising particles over a wide range of sizes, which particles have substantially uniform chemical properties. The phrase "substantially uniform chemical properties" is demonstrated by any one of three chemical parameters of uniformity characterizing the chemical composition of discrete particles within an assembly of particles having sizes, that is, diameters, within a range from about 25 microns to about 175 microns. As a first parameter of uniformity, the concentration of the mixture of deposited compounds within the catalytic material, defined as a weight ratio $R_a$ of expression I, varies from particle-to-particle within a range of plus or minus about five percent from an average value, $\bar{R}_a$, for any discrete particle size over the defined range of particle sizes.

$$R_a = \frac{\text{Wt. of deposited compounds}}{\text{(Wt. of silica)} + \text{(Wt. of deposited compounds)}} \quad \text{(I)}$$

where $R_a = \bar{R}_a \pm 0.05\bar{R}_a$

As a second parameter of uniformity, the concentration of certain constituents within the mixture of deposited compounds attached to the silica support, defined as a weight ratio $R_b$ of expression II, varies from particle-to-particle within a range of plus or minus about three percent of an average value, $\bar{R}_b$, for any discrete particle size over the defined range of particle sizes. The presence of the oxide-of-vanadium constituent may be expressed as weight percent $V_2O_5$ and the presence of the sulfate-of-potassium constituent may be expressed as the sum of weight percent $SO_3$ and weight percent $K_2O$.

$$R_b = \frac{\text{Wt. \% } V_2O_5}{\text{Wt. \% } (SO_3 + K_2O + V_2O_5)} \quad \text{(II)}$$

where $R_b = \bar{R}_b \pm 0.03\bar{R}_b$

As a third parameter of uniformity, the relative amount of $SO_3$ to $K_2O$ within the mixture of deposited compounds, defined as the ratio $R_c$ of moles of $SO_3$ to moles of $K_2O$ of expression III, varies from particle-to-particle within a range of plus or minus about three percent from an average value $\bar{R}_c$ for any discrete particle size within the defined particle size range.

$$R_c = \frac{\text{moles } SO_3}{\text{moles } K_2O} \qquad (III)$$

where $R_c = \bar{R}_c \pm 0.03 \bar{R}_c$

BRIEF DESCRIPTION OF THE DRAWINGS

FIG. 1 is a plot showing variations in uniformity in the concentration of deposited compounds contained within the catalyst, for a sample of catalyst of the invention as compared to commercially-available catalysts.

FIG. 2 is a plot showing variations in uniformity in the ratio of certain constituents within the mixture of deposited compounds attached to silca support, for a sample of the catalyst of the invention as compared to commercially-available catalysts.

DETAILED DESCRIPTION OF THE INVENTION

The process for preparing the catalytic material has the advantage of requiring only one impregnating step to achieve effective impregnation of catalytically active compounds within the pores of the silica support. Moreover, the process is advantageous in that there are no significant preferential losses of starting materials or intermediates during preparation of the catalytic material. Hence, the composition of the final catalyst can be computed from the amounts of ingredients used initially. Catalytic material prepared by the process is particularly suitable as an oxidation catalyst for converting naphthalene to phthalic anhydride and typically provides initial yields in excess of about 100 pounds phthalic anhydride per 100 pounds naphthalene feed. The catalytic material has relatively high oxidative activity, has excellent fluidizability, and usually requires no pre-conditioning prior to its use in a reactor.

The term "oxide-of-vanadium constituent" is intended to embrace the known vanadium oxide compounds in which vanadium is present with oxidation states of +3 to +5. The predominant oxide of vanadium present in the catalytic material is believed to be vanadium pentoxide, also known as vanadic oxide, $V_2O_5$, with minor amounts of reduced vanadium usually present. Vanadium pentoxide is present in the deposited mixture of compounds in an amount in a range from about 12 weight percent to about 18 weight percent, based upon the total weight of all compounds present in the mixture of deposited compounds attached to the support. Preferably, vanadium pentoxide is present in an amount in a range from about 15.5 weight percent to about 16.5 weight percent.

The term "sulfate-of-potassium constituent" is a generic phrase intended to include such compounds as potassium sulfate ($K_2SO_4$), potassium hydrogen sulfate ($KHSO_4$) and potassium pyrosulfate ($K_2S_2O_7$). Within the mixture of deposited compounds attached to the silica xerogel support, potassium pyrosulfate predominates, there being present minor amounts of other sulfates of potassium. The total amount of sulfates of potassium within the deposit of compounds may be expressed as the mole ratio of $SO_3$ to $K_2O$. A useful $SO_3$ to $K_2O$ mole ratio range is about 1.7 to one to about 2.1 to one. A mole ratio of $SO_3$ to $K_2O$ of about 1.80 to one to about 1.95 to one is preferred.

The terms "deposit of compounds", "deposited compounds", "mixture of deposited compounds", and "deposited mixture of compounds", are used interchangeably herein to describe the material contained substantially within the pores of the silica support.

Material suitable as a support may be characterized as a silica xerogel. Preferred as silica support is microspheroidal material of high porosity and high purity. Suitable material may be prepared by methods shown in U.S. Pat. No. 3,507,810. It is preferred that such materials be further treated by washing with mildly acidic solutions.

The term "silica gel" as used herein is a spray-dried hydrogel of silica having about 8 to 15 percent by weight water, that is, a product that has not been completely dried. Silica gel suitable for processing into silica xerogel support material is available from several commercial sources. It is preferred that such silica gel be relatively pure. It is expected, however, that silica gel prepared from a water-washed precipitate of sodium silicate and sulfuric acid will likely contain sodium sulfate or sodium bisulfate as impurities fairly evenly distributed among the silica gel particles within the pores of the particles. Suitable silica gel should not contain aluminum and sodium contaminants, detected as solubles in 4 N $H_2SO_4$, at levels greater than 0.05 weight percent, although useable materials may contain up to 0.5 percent aluminum and sodium contaminants with consequently lower product yields.

Commercial grade silica gels prepared by spray drying typically contain about 10 weight percent water and may usually require additional treatment to render them suitable for catalytic material support. Such treatment usually involves a drying step or a calcining step at temperatures and for periods of time dependent upon the preparation history of a particular silica gel. Temperatures as low as 150° to 200° C. may be used, although drying times as long as 16 hours may be required. Typically, silica gel is calcined at a temperature in a range from about 450° C. to about 460° C. for a period of about 0.5 to four hours. Either drying or calcining of silica gel can be utilized to provide silica xerogel suitable for making the catalytic material, depending upon the source of the silica gel, its physical and chemical properties and its preparation history.

An individual particle of suitable silica xerogel, microspheroidal in shape, is known to be an agglomeration of smaller spherical particles about 100 Å in diameter. Another parameter for determining the suitability of the microspheroidal silica xerogel as catalytic material support is pore volume (PV). A major portion of particle pore volume, as well as substantially all of the specific area, is attributable to the existence of interstitial spaces between packed spherical particles. A minor portion of the pore volume may be provided by spaces left by spherical particles missing from the packed agglomeration of spheres.

Suitable silica xerogel support material is characterized in having a pore volume in a range from about 0.75 cc/g to about 1.25 cc/g, with a preferred range being about 1.00 cc/g to about 1.20 cc/g. A suitable silica gel pore volume to be used initially in preparation of the catalyst may be determined by subtracting from a desired pore volume of the final catalyst both the pore volume occupied by the deposited mixture of compounds and the pore volume lost in processing (i.e., by pore "collapse"). Typically, the pore volumes of the final catalyst and that occupied by the deposited mixture of compounds can be calculated, while pore volume lost in processing must be determined experimentally. An expression for the relationship between pore volume of the catalyst, the pore volume of the silica gel both before and after processing, and the weights of the catalyst constituents, is as shown in Equation IV:

$$PV_{cat} = W_{SG}(PV_{SG} - PV_{Lost}) - \frac{W_{DC}}{2.44} \qquad (IV)$$

wherein
$PV_{cat}$ = Pore volume of final catalyst as desired
$PV_{SG}$ = Pore volume of silica gel before impregnation
$PV_{Lost}$ = Pore volume of silica gel lost in preparing catalyst
$W_{SG}$ =

$$\frac{\text{Wt. \% Silica used}}{100}$$

$W_{DC}$ = Weight of mixture of deposited compounds as expressed by $$\frac{\text{Wt. \% } (V_2O_5 + K_2O + SO_3)}{100}$$

It is an advantage provided by the process for preparing catalyst of the invention that the concentrated impregnating solution can be utilized in one step to impregnate silica materials having a pore volume as low as 0.75 cc/g.

Determination of the pore volume of silica xerogel support material is required prior to its impregnation. One method for determining pore volume involves a determination made on silica gel after calcination at 350° C. for two hours as described by W. B. Inness, *Analytical Chemistry*, 28 332 (1956).

Useful catalytic material contains the deposit of compounds in an average concentration within a range from about 20 weight percent to about 40 weight percent based upon the total weights of the silica xerogel support and of the deposit of compounds attached to the support. Preferably, the deposit of compounds is present in an average concentration within a range from about 32 weight percent to about 37 weight percent of the total weight of the catalytic material.

The aqueous solution of three salts, namely, vanadyl oxalate, potassium sulfate and potassium bisulfate, utilized for impregnating the silica xerogel support may be prepared by various methods. The vanadyl oxalate component, for example, may be prepared by firstly adding vanadium pentoxide to water to form a slurry, then heating the slurry to about 90° C., and thereafter adding oxalic acid slowly to the slurry while maintaining the temperature of the slurry-solution mixture at about 90° C. Or, the vanadyl oxalate component may be prepared by mixing together in incremental amounts vanadium pentoxide and oxalic acid simultaneously in the presence of water preheated to about 90° C. and thereafter maintaining the temperature of the mixture at about 90° C. for a period of time sufficient to effect reaction between vanadium pentoxide and oxalic acid. Or, oxalic acid may be dissolved in water, then heated to about 90° C. and thereafter vanadium pentoxide may be added slowly to the heated oxalic acid solution.

Each of the foregoing modes of vanadyl oxalate preparation is further characterized by a step of holding the prepared vanadyl oxalate solution at a temperature and for a period of time sufficient to obtain stabilization of the solution. The term "stabilization" characterizes, for example, a vanadyl oxalate solution which has been maintained at about 90° C. for approximately one hour. The vanadyl oxalate solution is then cooled to about 60° C., or lower. Concentrated (90–98%) sulfuric acid at a temperature of about 25° C. is then added, preferably adiabatically, to the vanadyl oxalate solution, with the oxalate solution at a temperature initially in a range from about 23° C. to about 60° C. With the addition of $H_2SO_4$, an exothermic reaction occurs so that the temperature of the solution may rise as much as 30° C., depending upon the rates of acid addition and loss of heat from the solution. Thereafter, potassium sulfate is added, preferably adiabatically, to the vanadyl oxalate-sulfuric acid solution whereby the potassium bisulfate component is formed in the water solution. Addition of $K_2SO_4$ results in an endothermic reaction so that the temperature of the solution could drop as much as 30° C.; hence, heat must usually be supplied to maintain the solution temperature at about 60° C. Alternatively, the sulfuric acid and potassium sulfate may be added simultaneously, in an adiabatic manner, to the vanadyl oxalate solution, so that the exothermic and endothermic reactions may be in balance. As another acceptable variation in the preparation method, a mixture of potassium bisulfate and potassium sulfate may be added to the vanadyl oxalate solution in place of the sulfuric acid-potassium sulfate addition. The hygroscopic property of potassium bisulfate, however, makes quantitative addition of the bisulfate salt to the solution more difficult. In any of these modes of preparation, it is a further requirement that after addition of potassium sulfate, the resulting solution be maintained at least about 60° C. by application of heat, if necessary, for a period of time, generally about 0.5 to 1.5 hours, sufficient to effect a stable solution. In the absence of such step, unstable solutions may result.

Bringing together suitable amounts of vanadium pentoxide, oxalic acid, sulfuric acid or potassium bisulfate, and potassium sulfate in accordance with the foregoing generally-described procedures provides a stable aqueous medium or solution containing vanadyl oxalate, potassium bisulfate and potassium sulfate. These compounds are typically present in water solution in a total amount of about 50 weight percent of the total weight of the solution with the solution having a pH of about 1.3. It is a characterizing feature of the invention that by use of preferred methods of preparation, this solution, without further dilution, remains stable for months at room temperature (about 23° C.). Although the solubilities of the principal compounds, namely, $VOC_2O_4$, $KHSO_4$ and $K_2SO_4$, are not exceeded in the aqueous solution, it would be expected that other less soluble compounds, such as potassium hydrogen oxalate ($KHC_2O_4$) and other complex potassium oxalates, would form precipitates in the undiluted aqueous solution. Surprisingly, the undiluted aqueous solution is stable, there being no detectable precipitates of compounds of the latter-mentioned type for a substantial period of time. The unexpected stability of the solution may be attributed to one or more of the aforementioned features of the method for preparing the aqueous impregnation solution.

Typically, the undiluted aqueous solution, the "concentrate", contains the three principal salts in concentration ranges of about 0.98 to about 1.18 moles/liter for vanadyl oxalate, about 3.26 to about 4.20 moles/liter for potassium bisulfate, and about 0.09 to about 0.47 moles/liter for potassium sulfate.

In a preferred preparation of the impregnating solution, the vandyl oxalate solution is firstly prepared in accordance with Equation V:

$$V_2O_5 + 3H_2C_2O_4 \cdot 2H_2O \rightarrow 2VOC_2O_4 + 2CO_2 + 5H_2O \quad (V)$$

A "standard" impregnating solution was prepared, for example, to contain 91.1 lb $VOC_2O_4$, 277.1 lb $KHSO_4$ and 31.77 lb $K_2SO_4$ in water to a total solution volume of about 67 gallons. Such solution had a density of 12.2 lb/gal at 23° C., with a mole ratio of $SO_3$-to-$K_2O$ of about 1.85-to-one. An investigation was carried out as to the stability of the impregnating solution of the invention by preparing various solutions having certain deviations from the aforementioned "standard" solution. Table 1 contains these deviations and corresponding stability characteristics.

TABLE I

| Deviation from Standard Soln. | Stability Characteristics | |
|---|---|---|
| | Days Stable @ 23° C. | Precipitate |
| None | >38 | — |
| 62 gal volume | >4 to <14 | $K_3H(SO_4)_2$ |
| 1% deficiency of oxalic acid | >29 | — |
| 5% deficiency of oxalic acid | >14 to <29 | $V_2O_5$ (apparently) |
| 5% excess of oxalic acid | >39 | — |
| 10% excess of oxalic acid | >6 to <21 | small amount of unknown |
| 10% excess of oxalic acid @ 62 gal. vol. | >6 to <21 | $KH_3(C_2O_4)_2 \cdot 2H_2O$ + $KHC_2O_4$ |
| 5% excess of oxalic acid @ $SO_3/K_2O$ = 1.80 (excess $K_2SO_4$) | >4 to <19 | $K_3H(SO_4)_2$ |
| 5% excess of oxalic acid @ $SO_3/K_2O$ = 1.95 (excess $H_2SO_4$) | >34 | — |

Prior to impregnating the silica support, the aqueous solution is usually diluted with water in an amount to provide a volume of about 98 percent of the total pore volume of the silica support to be impregnated. Impregnation of the silica support is accomplished by adding and mixing the aqueous solution into the silica material. The adding and mixing steps can be performed batchwise or by a continuous process. Practically any conventional mixing apparatus may be used, with those having stainless steel or glass lining being preferred. Examples of suitable mixing devices include Pfaudler or Abbe rotary mixers, V-type blenders and drum mixers, provided such mixers do not grind the silica xerogel particles to a finer size during mixing.

The adding step may be performed with the salt solution and silica components at a temperature in a range from about room temperature to about 60° C. An exothermic reaction occurs, due to the heat of wetting, when the components are brought together. Mixing usually proceeds for about 30 to about 60 minutes so as to provide a dry-appearing, free-flowing powder. It is a characteristic of the silica xerogel, made in accordance with the previous description, that the silica support has little or no tendency to shatter during the impregnation step.

A volume ratio of 0.98-to-1.00 of impregnating solution volume to silica xerogel pore volume is preferred inasmuch as the resulting impregnated material is in the form of a dry-appearing, free-flowing powder. Useable catalytic material may be obtained, however, from powders prepared with differing volume ratios. At a volume ratio of above 1.00-to-1.00, the resulting material will likely appear damp and lack the desirable free-flowing property. Useable catalytic materials may be prepared utilizing a higher ratio of impregnating solution volume to silica xerogel pore volume, although at such high ratio the absence of the free-flowing property of the impregnated powder will likely cause material-handling problems. Volume ratios as low as 0.90-to-1.00 may also provide useable catalytic materials, although at such low ratio there will likely result an increase in amounts of unimpregnated silica.

Drying before calcining of the solution-impregnated silica xerogel is optional for removal of the bulk of the water from the material. In a typical drying step carried out at about 140° C. at about atmospheric pressure, about 90 percent of the water added to the silica xerogel during the impregnating step is removed. Drying may be performed in air at either atmospheric pressure or at reduced pressure, i.e., as low as 100 torr absolute. The temperature and time period under which the material is dried relates to the pressure under which drying takes place. In using any rotary drier, care should be taken in drying the solution-impregnated material so as to avoid formation of cold spots in the mass where water may condense.

Calcining of the dried solution-impregnated silica xerogel material in air is required for conversion of the material into catalytically active material. For example, during the calcination step, the oxalate component decomposes to carbon monoxide and carbon dioxide; a large proportion of the potassium bisulfate converts to potassium pyrosulfate; and most of the vanadium(IV) is oxidized to vanadium(V). Calcining is performed by heating the solution-impregnated silica xerogel in air at a temperature in a range from about 350° C. to about 390° C. for a period of about 30 minutes to about two hours. Calcining at about 350° C. is preferred, usually occurring at atmospheric pressure, and may be carried out in a rotary calciner or a porcupine processor. Care must be taken during the calcining step to maintain uniform calcination temperatures so that preferential losses of $SO_3$ are minimized. Under laboratory conditions, temperatures may be easily controlled so that no measurable losses of $SO_3$ occur between 350° and 390° C. With commercial-scale equipment, shell temperatures of a rotary calciner may reach high enough to cause losses of about two percent of the $SiO_3$ component in the catalyst. Hence, this small loss should be compensated for by the addition of a small amount of excess $H_2SO_4$ during preparation of the impregnating solution.

Useful catalytic material may comprise several particle size fractions depending upon the characteristics of the reactor and parameters of the process utilized. Typically useful catalytic materials comprise at least 90 weight percent of particles having diameters in a range from about 20 micron to about 300 microns. An assembly of particles having sizes from about 25 microns to about 175 microns is preferred.

Catalytic material of the invention is characterized in having substantially uniform chemical composition, especially as compared to commercially-available catalysts. In order to demonstrate the superiority of catalyst of the invention over commercial catalysts, chemical analyses were made for uniformity of the catalyst actually prepared in accordance with the procedures of Example I herein and for uniformity of the only known commercially-available catalysts used for oxidizing naphthalene to phthalic anhydride. The commercially-available catalysts were Aerogel PAA-3 catalyst sold by American Cyanamid Co., Wayne, N.J., and Davison Grade 906 catalyst sold by Davison Chemical Div. of W. R. Grace, Baltimore, Md. These chemical analyses consisted firstly of a determination of the uniformity in concentration of deposited compounds contained within the catalyst samples, defined herein as $R_a$, for fractions of several different particle sizes of the catalysts over a range of sizes from about 25 microns to about 175 microns. Secondly, the catalyst samples were analyzed for uniformity in composition of the constituents making up the deposited compounds attached to the silica support, defined herein as $R_b$. Thirdly, the catalyst samples were analyzed for uniformity of the sulfate-of-potassium constituent of deposited compounds, defined herein as $R_c$. The amounts of the oxide-of-vanadium and sulfate-of-potassium constituents of the deposited compounds, expressed as weight percent of $V_2O_5$, $K_2O$ and $SO_3$, were determined by X-ray fluorescence methods.

Data derived from the comparative analyses are summarized in Table II. The data show that for each of the three parameters of uniformity, the catalyst of the invention is clearly superior to the commercial catalysts. For example, as to uniformity in concentration of deposited compounds, catalyst of the invention has deviations from an average value over the particle size range, $\bar{R}_a$, from +2 percent to −3 percent of $\bar{R}_a$. In comparison, the commercial catalysts have deviations ranging from −50 percent to +50 percent of $\bar{R}_a$. As to uniformity in composition of the deposited compounds, catalyst of the invention has deviations from an average value over the particle size range, $\bar{R}_b$, within ±2 percent of $\bar{R}_b$. The commercial catalysts have deviations ranging from −30 percent to +23 percent of $\bar{R}_b$. As to uniformity in the presence of the sulfate-of-potassium constituent within the deposited compounds as expressed by the mole ratio of $SO_3$ to $K_2O$, catalyst of the invention has deviations from an average value over the particle size range, $\bar{R}_c$, within ±2 percent of $\bar{R}_c$. The commercial catalysts have deviations ranging from −12 percent to +18 percent of $\bar{R}_c$.

The superior uniformity in chemical composition of catalyst of the invention over commercial catalysts is clearly illustrated in the drawing figures. In FIG. 1, variations in uniformity of concentration of deposited compounds are plotted over the range of particle sizes of the catalysts. In FIG. 2, variations in uniformity of the composition of the deposited compounds, as determined by a measure of the amount of oxide-of-vanadium (expressed as weight percent $V_2O_5$) in the total amount of deposited compounds (expressed as the sum of the total weight percent amounts of $SO_3 + K_2O + V_2O_5$), are plotted over the range of particle sizes. A most desirable catalyst would be one having perfect uniformity of concentration and composition parameters across the range of particle sizes. Such perfect uniformity would be theoretically represented by a horizontal straight line in FIGS. 1 and 2. As shown in the drawing figures, catalyst of the invention very nearly approaches perfect uniformity relative to the commercially-available catalysts.

Catalytic material of the invention is also characterized in having high attrition resistance, that is, the property of resistance of larger particles breaking into finer particles. Attrition of catalytic material is costly in terms of reduction of catalyst life. Attrition resistance may be determined generally in accordance with a published method [Forsythe et al., "Attrition Characteristics of Fluid Cracking Catalysts", *Ind. Eng. Chem.*, 41, 1200–1205 (1949)]. The "attrition index" (A.I.) of catalytic material may be defined as follows:

$$A.I. = \frac{\Delta f \%/\text{hr}}{\% P} \times 100$$

wherein $\Delta f$ is weight percent increase per hour of fines, wherein "fines" means particles measured by weight having diameters less than about 20 microns, and %P is the percent particles by weight of the initial charge of catalytic material to be tested, which particles have diameters greater than about 20 microns; a lower attrition index indicates better resistance to attrition. Comparative attrition tests were made for the catalytic material of the invention as compared to samples of commercially-available catalysts. Tests were made on samples of freshly calcined catalytic material, uniformly calcined at about 350° C. for about two hours, with fluidization furnished by dry air from a compressed air source. Attrition index data for samples of the catalyst of the invention ranged from 4 to 8, as described in the following working examples. By comparison, attrition index data for commercially-available catalysts ranged from about 9 for American Cyanamid Aerogel PAA-3 catalyst to about 17 for Davison Grade 906 catalyst.

Catalytic material prepared in accordance with the invention exhibits superior operating characteristics when utilized to convert naphthalene to phthalic anhydride, especially in oxidation processes utilizing naphthalene derived from coal tar. The catalytic material may be used with advantage in known commercial naphthalene-to-phthalic anhydride oxidation processes. U.S. Pat. No. 3,852,308 to Ryder et al. discloses a process particularly suited to utilization of the catalytic material. The subject matter of the Ryder '308 patent, which describes useful operating parameters and equipment, is incorporated herein by reference.

A typical commercial scale reactor for conversion of naphthalene to phthalic anhydride has a vertically-oriented cylindrically-shaped fluid-bed reaction zone 13 feet in diameter and about 35 feet in height under operating conditions when the catalytic material is in a fluidized state. For a reactor of described dimensions, approximately 120,000 pounds of oxidation catalyst is contained in the reaction zone. Liquid naphthalene is introduced into the base of the reaction zone and is mixed with air in the reactor to form a gaseous stream containing air and naphthalene vapor. Flow of the gaseous stream through the reaction zone provides the means for sustaining the catalytic material in a dense fluidized state characterized by a fluid density of about 25 lbs/cu.ft. The velocity of the gaseous stream, correcting for the velocity in the void fraction of the bed, is in a range from about 0.4 to about 5.0 feet per second. A preferable stream velocity lies in a range from about 0.5 to about 2.0 feet per second for the described reactor. For an acceptable throughput and catalyst exposure, the average pressure within the fluidized catalyst bed should be at least about 25 p.s.i.g., and preferably be within a range of about 35 to about 500 p.s.i.g. The naphthalene feed rate for the described reactor can be as low as 3,500 pounds per hour or as high as 15,000 pounds per hour, althouth the preferred naphthalene feed rate is usually in a range from about 10,000 to about 12,000 pounds of naphthalene per hour. A corresponding naphthalene loading for the preferred feed rate for the reactor containing the specified amount of catalyst is in a range from about 0.08 to about 0.10 pounds of naphthalene per hour per pound of catalyst. Another parameter affecting conversion of naphthalene to phthalic anhydride is the relative amounts of air and naphthalene in the gaseous stream. Generally, an air-to-naphthalene weight ratio in a range from about 6 to 1 to about 12 to 1 may be suitable. An air-to-naphthalene mixture in a weight ratio range of about 7 to 1 to about 9 to 1 is preferred, especially in oxidation processes utilizing relatively high fluid bed pressures. Oxidation of naphthalene to phthalic anhydride is preferably carried out at a fluid bed temperature which provides minimal amounts of under-oxidized by-product, such as naphthoquinone, or over-oxidized by-product, such as maleic anhydride. Typically, such an optimum temperature lies in a range from about 320° C. to about 400° C.; a preferred optimum range is from about 340° C. to about 390° C. An oxidation process which utilizes catalytic material of the invention in the described reactor may be expected initially to provide a yield of at least about 100 pounds phthalic anhydride per 100 pounds of naphthalene feed.

The following working examples are presented to exemplify preparation and use of catalytic material in accordance with the process of the invention. These examples are not to be construed as limiting the claims to the procedures set forth in the examples, inasmuch as there are numerous variations and modifications possible. All parts and percentages of the examples as well as throughout the specification are by weight unless otherwise indicated.

EXAMPLE I

To a glass-lined vessel containing about 1.5 l of water, there was added about 389 g of vanadium pentoxide (Foote Mineral Co., Purified Grade, Exton, Pa.) to form a slurry. The slurry was heated to about 90° C. over a period of about one hour, after which time about 810 g of oxalic acid dihydrate ($H_2C_2O_4 \cdot 2H_2O$) (J. T. Baker Chemical Co., Reagent Grade, Phillipsburg, N.J.) was added slowly and with mixing over a 40-minute period. The mixture was maintained at a temperature of about 90° C. for about one hour with mixing and then allowed to cool to room temperature with the aid of an ice bath without mixing. Then 667 g of 95.9% sulfuric acid (J. T. Baker Co., Reagent Grade) was added adiabatically with stirring to the mixture. With the temperature being maintained between about 60° C. and 70° C. by heating of the mixture, about 1370 g of potassium sulfate (J. T. Baker Co., Reagent Grade) was added over a period of about 15 minutes with stirring being maintained until all components were in solution. The solution was maintained in the same temperature range for about one hour and then the solution was cooled to room temperature with the aid of an ice bath and then diluted with water to a final volume of about 3.4 l to provide an impregnating solution.

Silica gel obtained from American Cyanamid Co., Ft. Worth, Texas, and made in accordance with procedures similar to those described in U.S. Pat. No. 3,507,810, was calcined for about four hours at about 450° C. in an air atmosphere at about atmospheric pressure to form a silica xerogel. The xerogel was then cooled and purified by successive washings with dilute sulfuric acid and water. The washed silica xerogel was then dried in trays in an oven at a temperature of about 150° C. for about 62 hours. The amounts of soluble contaminants in the silica material were then determined to be at levels of 0.03 percent aluminum and 0.01 percent sodium. The pore volume of the silica xerogel was determined to be about 0.84 cc/g. About 3900 g of the silica xerogel was placed in rotary evaporator. The xerogel was turned in the evaporator while about 3112 ml of the previously prepared impregnating solution was added slowly to the xerogel over a period of 23 minutes. Mixing was continued for about 70 minutes after addition of the impregnation solution. There resulted a dry-appearing free-flowing powder. Mixing was then continued with heating for a further period of 180 minutes with the temperature of the powder gradually increasing to about 140° C. to provide a blue-colored powder. The powder was placed in partially covered glass trays in a forced air oven and calcined at 350° C. for about two hours. The calcined catalyst had a golden orange color, an attrition index of 4.0 and a mean pore diameter of 68 Å. Analyses of screened fractions showed that the catalyst had a uniform composition (see Table II).

TABLE II

Comparisons of Uniformity Between Commercially-Available Catalysts and Catalyst of the Invention

| Catalyst Type | Representative Particle Size of Fraction (μm) | Concentration of Deposited Compounds | | Composition of Deposited Compounds | | | |
|---|---|---|---|---|---|---|---|
| | | $R_a$ (Wt. %) | Deviation from $R_a$ (%) | $R_b$ | Deviation from $R_b$ (%) | $R_c$ | Deviation from $R_c$ (%) |
| American | 175 | 28.5 | −26 | 0.195 | +23 | 2.04 | +2 |
| Cyanamid | 105 | 30.9 | −20 | 0.165 | +4 | 2.08 | +3 |
| Aerogel | 60 | 40.6 | +5 | 0.163 | +3 | 1.91 | −5 |
| PAA-3 | 25 | 54.1 | +41 | 0.110 | −30 | 2.01 | 0 |
| | Ave. | $R_a = 38.5$ | | $R_b = 0.158$ | | $R_c = 2.01$ | |
| Davison | 175 | 15.1 | −50 | 0.157 | −3 | 2.52 | +18 |
| Chemical | 105 | 27.2 | −10 | 0.155 | −5 | 2.14 | +1 |
| Div. | 60 | 33.7 | +10 | 0.164 | +1 | 1.98 | −7 |
| Grade 906 | 25 | 45.8 | +50 | 0.174 | +7 | 1.86 | −12 |
| | Ave. | $R_a = 30.5$ | | $R_b = 0.163$ | | $R_c = 2.13$ | |
| Example I- | 175 | 33.9 | −3 | 0.169 | −2 | 1.91 | 0 |
| Catalyst | 105 | 35.2 | 0 | 0.171 | 0 | 1.90 | 0 |
| of the | 60 | 35.5 | +1 | 0.175 | +2 | 1.87 | −2 |
| Invention | 25 | 35.8 | +2 | 0.172 | 0 | 1.94 | +2 |
| | Ave. | $R_a = 35.1$ | | $R_b = 0.172$ | | $R_c = 1.91$ | |

EXAMPLE II

The catalytic oxidation of naphthalene to phthalic anhydride utilizing the catalytic material prepared by Example I was demonstrated as follows. About 4426 g of the catalytic material was placed in a pilot-plant size carbon steel reactor having dimensions 2 inches in diameter and 12 feet in length. Desulfurized coal-tar naphthalene was introduced into the reactor at a feed concentration in air of 3.0 mole percent at a pressure of about 5 psig. Average contact time was 8 seconds for a 10-day test period. Optimum yield of phthalic anhydride was 102.5 pounds per 100 pounds of naphthalene feed at a reactor temperature of about 340° C. The product stream also contained 1.9 pounds maleic anhydride and 1.4 pounds naphthoquinone per 100 pounds naphthalene feed.

EXAMPLE III

A steel-lined tank was filled with 280 gallons of water and heated with agitation to about 188° F. Over a period of 45 minutes and with the temperature of the solution maintained between 188°–196° F., a total of 356 pounds of vanadium pentoxide (Union Carbide Co., High Purity Grade, special lot low chromium, New York, N.Y.) and 743.5 pounds oxalic aci dihydrate (Allied Chemical Co., Tech. Grade, Morristown, N.J.) were added in incremental amounts to the tank in the following manner: Firstly, about 62.5 pounds $V_2O_5$ was added and stirred into the water, then about 100 pounds oxalic acid was added with stirring. After reaction subsided visibly, the balance of the $V_2O_5$ and oxalic acid components were added incrementally in a likewise manner. The solution was then maintained under agitation at a temperature between about 190°–200° F. for about one hour. Then over a period of about one-half hour, 460 pounds 93% $H_2SO_4$ was added slowly in two increments of 230 pounds each to the agitating solution. After addition of the first increment of $H_2SO_4$, the temperature was observed to increase from about 150° F. to about 162° F.; after addition of the second increment the temperature increased to about 174° F. Then 300 pounds of $K_2SO_4$ (Mallinckrodt Co., Purified Grade, St. Louis, Mo.) was added to the solution and thereafter a third 230 pound increment of $H_2SO_4$ was added; after the third increment, the temperature was observed to be 175° F. Then over a period of about 20 minutes, about 1050 pounds $K_2SO_4$ was added to the agitating solution in three increments of 300 pounds and a final increment of 150 pounds. During the $K_2SO_4$ addition period, the temperature of the solution was observed to decrease from about 162° F. to about 140° F. The solution was held at a temperature of about 140° F. for about 30 minutes and then cooled to 130° F.

Commercially available silica gel (prepared by American Cyanamid Co., Ft. Worth, Texas) was calcined for about 40 minutes in a rotary kiln having a hot zone shell temperature of about 1100° F. under atmospheric pressure and with an air purge to form a silica xerogel. The amounts of soluble contaminants in the silica material were determined to be as follows:

| Wt. % | Lot A | Lot B | Average |
|---|---|---|---|
| Na | 0.010 | 0.008 | 0.009 |
| Al | 0.105 | 0.036 | 0.071 |
| Fe | 0.015 | 0.014 | 0.015 |

The pore volume of the silica xerogel was determined to be about 1.15 cc/g. About 700 pounds of the silica xerogel was placed in a double cone vacuum dryer along with approximately 60 pounds of fine particulates accumulated during processing of the silica. The silica comprised particles in accordance with the following screen fractions: 97 percent of the particles were less than 100 mesh size, 35 percent were less than 200 mesh size, and 6 percent were less than 325 mesh size (Tyler mesh). Then about 960 pounds of the previously prepared impregnation solution was added to the xerogel and diluted with enough water to provide a ratio of solution volume to pore volume of about 0.98 to 1.00. The silica xerogel-water solution components were mixed in the dryer for about 30 minutes to provide a free-flowing dry-appearing powder. The powder was then calcined for about 40 minutes in a rotary calciner having a hot zone shell temperature of about 850° F. The calcined catalyst had a golden-orange color.

EXAMPLE IV

Five lots of catalytic material were prepared in accordance with the procedures outlined in Example III. A composite sample of the five lots was analyzed for uniformity as to the presence of sulfate-of-potassium and oxide-of-vanadium constituents in the deposited mixture of compounds on the silica particles for various fractions of screened particles, as set out in Table III. In a pilot-plant size carbon-steel reactor 2 inches in diameter and 12 feet in length, test runs were made for samples of each of the five lots with a final test run on a composite sample for all five lots. For each of the six test runs, about 4 kilograms of catalytic material was utilized in the reactor. An air-naphthalene mixture was introduced into the reactor at a naphthalene feed concentration of about 3.0 mole percent at a pressure of about 5 p.s.i.g. The average naphthalene-to-catalyst contact time for all test runs was about 8 seconds for the duration of test runs. Test run duration, optimum conversion temperatures, and yields of phthalic anhydride, maleic anhydride and naphthoquinone in the product stream, for the six test runs, are set forth in Table IV.

TABLE III

Uniformity of Deposited Compounds for Varying Particle Sizes

| Tyler Mesh Size | Wt. % Present | Oxide-of-Vanadium as $V_2O_5$ (Wt. %) | Sulfate-of-Potassium as | |
|---|---|---|---|---|
| | | | $K_2O$ (Wt. %) | $SO_3$ (Wt. %) |
| +140 | 17 | 5.50 | 11.3 | 17.0 |
| 140–200 | 35 | 5.54 | 11.3 | 17.1 |
| 200–270 | 22 | 5.55 | 11.4 | 17.4 |
| 270–325 | 10 | 5.54 | 11.5 | 17.2 |
| −325 | 16 | 5.52 | 11.2 | 16.9 |

TABLE IV

Phthalic Anhydride Yields for Commercial-Size Catalyst Batches

| Lot No. | Attrition Index | Quantity of Catalyst Produced (lb) | Days on Stream | Parameters at Optimum Cond. | | | |
|---|---|---|---|---|---|---|---|
| | | | | Temp. (°C.) | Yield (per 100 lbs. naphthalene) | | |
| | | | | | PAA | MAA | NQ |
| 1A | 6 | 17,500 | 20.5 | 343 | 103 | 1.5 | 2.0 |
| 1B | 7 | 20,000 | 18 | 343 | 101 | 1.7 | 0.8 |
| 2 | 6 | 30,750 | 6.75 | 338 | 102 | 2.2 | 1.5 |
| 3 | 6 | 36,000 | 13.75 | 338 | 102 | 1.7 | 1.2 |
| 4 | 8 | 28,500 | 34.75 | 348 | 104 | 1.6 | 1.7 |
| Composite of all lots | | 132,750 | 1 | 330 | 100 | 2.0 | 1.6 |
| | | | 20 | 343 | 102 | 1.6 | 1.5 |
| | | | 36.25 | 345 | 103.5 | 1.5 | 1.2 |

EXAMPLE V

Catalytic material prepared in accordance with the procedures of Example III was tested in a commercial-scale reactor. Approximately 109,000 pounds of the catalytic material was placed in the reactor. Under operating conditions a vertically-oriented fluidized bed reaction zone was established about 30 feet in height. Over a test period of about 14 days, naphthalene was introduced into the reactor in a range from 7,300 to 8,700 pounds of naphthalene per hour, at an air-naphthalene weight ratio in a range from about 8.3 to one to about 8.9 to one. Reactor zone operating temperatures ranged from 330° C. to about 350° C. Phthalic anhydride yield was about 100.2 pounds, while the yield of naphthalene was about 0.29 pounds, per 100 pounds of naphthalene feed.

Although specific examples of the instant invention have been set forth hereinabove, it is not intended that the invention be limited solely thereto, but is to include all the variations and modifications falling within the scope of the appended claims.

What is claimed is:

1. Catalytic material provided by a mixture of compounds deposited upon a silica support, said material prepared by a process comprising:
    adding an aqueous solution of salts, comprising vanadyl oxalate, potassium sulfate and potassium bisulfate, to porous silica support to form a substantially free-flowing dry-appearing salt-impregnated silica powder, the powder characterized in having substantially all of said salts contained within pores of the silica powder;
    whereby the salt-impregnated silica powder after calcining yields particles of catalytic material over a range of sizes, which particles are characterized in having a substantially uniform chemical composition.

2. The catalytic material of claim 1 wherein the process is further characterized by the step of forming the aqueous solution of salts by adding potassium sulfate to an acidic solution of water, vanadyl oxalate, and sulfuric acid or potassium bisulfate, or both, and immediately thereafter heating the acidic solution containing potassium sulfate to at least 60° C.

3. The catalytic material of claim 1 wherein the process is further characterized by the step of forming the aqueous solution of salts by adding an acidic solution of water, potassium sulfate and sulfuric acid or potassium bisulfate, or both, to vanadyl oxalate in the presence of water, and immediately thereafter heating the vanadyl oxalate-acidic solution to at least about 60° C.

4. The catalytic material of claim 1 wherein the process is further characterized by the step of preparing vanadyl oxalate in a solution by bringing together water, vanadium pentoxide and oxalic acid, and maintaining the solution at a temperature and for a period of time sufficient to obtain stabilization of the solution.

5. The catalytic material of claim 4 wherein the process is further characterized by the step of maintaining the solution at a temperature of about 90° C. for about one hour to obtain stabilization of the solution.

6. The catalytic material of claim 1 wherein the aqueous solution of salts contains from about 0.98 to about 1.18 moles per liter vanadyl oxalate; from about 3.26 to about 4.20 moles per liter potassium bisulfate; and from about 0.09 to about 0.47 moles per liter potassium sulfate.

7. The catalytic material of claim 1 wherein the process further comprises the steps of
    drying the salt-impregnated silica powder to remove free water; and
    calcining the salt-impregnated, dried silica powder in an air atmosphere at a temperature in a range from about 350° C. to about 400° C.;
    whereby there is provided a mixture of deposited compounds within the pores of the catalytic material, said mixture of deposited compounds consisting essentially of at least one oxide-of-vanadium constituent and at least one sulfate-of-potassium constituent.

8. The catalytic material of claim 7 wherein the process is further characterized in providing a calcined powder comprising from about 60 to about 80 weight percent of silica and from about 20 to about 40 weight percent of said mixture of deposited compounds derived from said aqueous solution.

9. The catalytic material of claim 8 wherein the process is further characterized by said mixture of deposited compounds containing potassium pyrosulfate and potassium sulfate, as expressed in a mole ratio range of $SO_3$ to $K_2O$, from about 1.7 to one to about 2.1 to one.

10. The catalytic material of claim 8 wherein the process is further characterized by said mixture of deposited compounds containing oxide of vanadium expressed as vanadium pentoxide from about 12 percent to about 18 percent of the total weight of said mixture of deposited compounds.

11. The catalytic material of claim 7 further characterized by the concentration of said mixture of deposited compounds in the catalytic material being defined as $$R_a = \frac{\text{Wt. of deposited compounds}}{(\text{Wt. of silica}) + (\text{Wt. of deposited compounds})}$$

with the proviso that the value of $R_a$ has a particle-to-particle variation within a range of plus or minus about five percent of an average value of $R_a$ for particles having sizes within a range from about 25 microns to about 175 microns.

12. The catalytic material of claim 7 further characterized by the relative concentration of said oxide-of-vanadium and said sulfate-of-potassium constituents being defined as $$R_b = \frac{\text{Wt. \% } V_2O_5}{\text{Wt. \% } (SO_3 + K_2O + V_2O_5)}$$

wherein the amount of oxide of vanadium present is expressed as $V_2O_5$ and the amount of sulfate of potassium present is expressed as the sum of $SO_3$ and $K_2O$, with the proviso that the value of $R_b$ has a particle-to-particle variation within a range of plus or minus three percent of an average value for $R_b$ for particles having sizes within a range from about 25 microns to about 175 microns.

13. The catalytic material of claim 12 further characterized by said sulfate-of-potassium constituent being present in said mixture of deposited compounds as expressed by the mole ratio of $SO_3$ to $K_2O$ defined as $$R_c = \frac{SO_3}{K_2O}$$

with the proviso that the value of $R_c$ has a particle-to-particle variation within a range of plus or minus about three percent of an average value $R_c$ for particles having sizes within a range from about 25 microns to about 175 microns.

14. A process for preparing a catalyst useful in vapor-phase fluid-bed catalytic oxidation of naphthalene to phthalic anhydride, the process comprising:
impregnating porous silica with an aqueous solution of salts comprising vanadyl oxalate, potassium sulfate and potassium bisulfate, by mixing together silica and said aqueous solution in amounts sufficient to provide a substantially free-flowing, dry-appearing powder;
calcining the powder in an air atmosphere at a temperature in a range from about 350° C. to about 400° C.;
whereby calcined powder is provided comprising particles of silica having a mixture of compounds deposited on the silica particles, said mixture of deposited compounds consisting essentially of at least one oxide of vanadium and at least one sulfate of potassium.

15. The process of claim 14 further characterized by the step of forming the aqueous impregnating solution by adding potassium sulfate to an acidic solution of water, vanadyl oxalate, and sulfuric acid or potassium bisulfate, or both, and immediately thereafter heating the acidic solution containing potassium sulfate to at least 60° C.

16. The process of claim 14 further characterized by the step of forming the aqueous impregnating solution by adding an acidic solution of water, potassium sulfate and sulfuric acid or potassium bisulfate, or both, to vanadyl oxalate in the presence of water, and immediately thereafter heating the vanadyl oxalate-acidic solution to at least about 60° C.

17. The process of claim 14 further characterized by the step of preparing vanadyl oxalate in a solution by bringing together water, vanadium pentoxide and oxalic acid, and maintaining the solution at a temperature and for a period of time sufficient to obtain stabilization of the solution.

18. The process of claim 17 further characterized by the step of maintaining the solution at a temperature of about 90° C. for about one hour to obtain stabilization of the solution.

19. The process of claim 14 wherein the aqueous impregnating solution contains from about 0.98 to about 1.18 moles per liter vanadyl oxalate; from about 3.26 to about 4.20 moles per liter potassium bisulfate; and from about 0.09 to about 0.47 moles per liter potassium sulfate.

20. The process of claim 14 wherein the average concentration of said mixture of deposited compounds is within a range from about 20 to about 40 weight percent of the total weight of said catalyst.

21. The process of claim 20 wherein said range is from about 32 to about 37 weight percent.

22. The process of claim 14 wherein said mixture of deposited compounds contains said oxide of vanadium in an average amount as expressed as vanadium pentoxide in a range from about 12 to about 18 weight percent of the total weight of said mixture of deposited compounds.

23. The process of claim 22 wherein said range is from about 15.5 to about 16.5 weight percent.

24. The process of claim 14 wherein said mixture of deposited compounds contains said sulfate of potassium as expressed as a mole ratio of $SO_3$ to $K_2O$ in a range from about 1.70 to one to about 2.10 to one.

25. The process of claim 14 wherein said mixture of deposited compounds contains sulfate of potassium in the form of potassium pyrosulfate and potassium sulfate as expressed as a mole ratio of $SO_3$ to $K_2O$ in a range from about 1.80 to one to about 1.95 to one.

26. The process of claim 14 wherein said calcined powder comprises about 99 percent by weight particles having a Tyler mesh size less than about 60 and about 85 to 90 percent by weight having a Tyler mesh size between about 60 and 325.

27. The process of claim 14 further characterized by the concentration of said mixture of deposited compounds within the catalyst being defined as $$R_a = \frac{\text{Wt. of deposited compounds}}{(\text{Wt. of silica}) + (\text{Wt. of deposited compounds})}$$

with the proviso that the value of $R_a$ has a particle-to-particle variation within a range of plus or minus about five percent of an average value of $R_a$ for particles having sizes within a range from about 25 microns to about 175 microns.

28. The process of claim 14 further characterized by the relative concentration of said oxide of vanadium and said sulfate of potassium within said mixture of deposited compounds being defined as $$R_b = \frac{\text{Wt. \% } V_2O_5}{\text{Wt. \% } (SO_3 + K_2O + V_2O_5)}$$

wherein the amount of oxide of vanadium present is expressed as $V_2O_5$ and the amount of sulfate of potassium present is expressed as the sum of $SO_3$ and $K_2O$, with the proviso that the value of $R_b$ has a particle-to-particle variation within a range of plus or minus three percent of an average value for $R_b$ for particles having sizes within a range from about 25 microns to about 175 microns.

29. The process of claim 28 further characterized by said sulfate of potassium being present in said mixture of deposited compounds as expressed by the mole ratio of $SO_3$ to $K_2O$ defined as $$R_c = \frac{SO_3}{K_2O}$$

with the proviso that the value of $R_c$ has a particle-to-particle variation within a range of plus or minus about three percent of an average value of $R_c$ for particles having sizes within a range from about 25 microns to about 175 microns.

* * * * *